(12) United States Patent
Shepherd

(10) Patent No.: US 11,497,758 B2
(45) Date of Patent: *Nov. 15, 2022

(54) METHOD OF TREATING OXIDATIVE STRESS DUE TO RADIATION EXPOSURE

(71) Applicant: Samuel L. Shepherd, Leesville, SC (US)

(72) Inventor: Samuel L. Shepherd, Leesville, SC (US)

(*) Notice: Subject to any disclaimer, the term of this patent is extended or adjusted under 35 U.S.C. 154(b) by 0 days.

This patent is subject to a terminal disclaimer.

(21) Appl. No.: 17/378,079

(22) Filed: Jul. 16, 2021

(65) Prior Publication Data

US 2022/0288097 A1    Sep. 15, 2022

Related U.S. Application Data

(63) Continuation of application No. 16/683,996, filed on Nov. 14, 2019, now Pat. No. 11,065,269.

(60) Provisional application No. 62/767,648, filed on Nov. 15, 2018.

(51) Int. Cl.
| | | |
|---|---|---|
| *A61K 31/7034* | (2006.01) | |
| *A61K 9/00* | (2006.01) | |
| *A61K 47/44* | (2017.01) | |

(52) U.S. Cl.
CPC ........ *A61K 31/7034* (2013.01); *A61K 9/0014* (2013.01); *A61K 9/0053* (2013.01); *A61K 47/44* (2013.01)

(58) Field of Classification Search
CPC .............. A61K 31/7034; A61K 9/0014; A61K 9/0053; A61K 47/44
See application file for complete search history.

(56) References Cited

U.S. PATENT DOCUMENTS

| | | |
|---|---|---|
| 6,022,701 A | 2/2000 | Boussiba et al. |
| 7,063,957 B2 | 6/2006 | Chen |
| 8,937,099 B2 | 1/2015 | Goldstein |
| 9,464,106 B2 | 10/2016 | Kauppinen et al. |
| 9,707,239 B2 | 7/2017 | Kassis et al. |
| 10,703,701 B2 | 7/2020 | Hinman et al. |
| 2003/0064955 A1 | 4/2003 | Prasad et al. |
| 2004/0077036 A1 | 4/2004 | Thomas et al. |
| 2005/0124032 A1 | 6/2005 | De La Fuente Moreno et al. |
| 2010/0285557 A1 | 11/2010 | Martin et al. |
| 2018/0303767 A1 | 10/2018 | Miller |

OTHER PUBLICATIONS

Hama et al., J. Pharm. Sci., 2012, 101, p. 2909-2916. (Year: 2012).*
Matsushita et al., Fisheries Science, 2000, 66, p. 980-985. (Year: 2000).*
Yokoyama et al., Journal of Natural Products, 1995, 58(12), p. 1929-1933. (Year: 1995).*

* cited by examiner

*Primary Examiner* — Jonathan S Lau
(74) *Attorney, Agent, or Firm* — Egbert, McDaniel & Swartz, PLLC

(57) ABSTRACT

A method of treating a subject afflicted with oxidative stress due to radiation exposure has the steps of preparing glucosidic astaxanthin by reacting astaxanthin with a monosaccharide, and administering a therapeutic amount of the glucosidic astaxanthin to the subject in need of such treatment. The astaxanthin is reacted with the monosaccharide at a microwave frequency of between 1 and 100 GHz for at least one second and no more than 25 seconds. The glucosidic astaxanthin can be added to a carrier material.

10 Claims, No Drawings

METHOD OF TREATING OXIDATIVE STRESS DUE TO RADIATION EXPOSURE

RELATED U.S. APPLICATIONS

The present application is a continuation-in-part of U.S. patent application Ser. No. 16/683,996, filed on Nov. 14, 2019, and entitled "Method of Using Astaxanthin for the Treatment of Diseases, and More Particularly, the Treatment of Cancer", now U.S. Pat. No. 11,065,269, issued on Jul. 20, 2020. U.S. patent application Ser. No. 16/683,996 claimed priority from U.S. Provisional Patent Application Ser. No. 62/767,648, filed on Nov. 15, 2018 and entitled "Method of Using Astaxanthin for the Treatment of Diseases, and More Particularly, the Treatment of Cancer".

BACKGROUND OF THE INVENTION

1. Field of the Invention

The present invention relates to treating disease. More particularly, the present invention relates to methods for the treatment and reduction of oxidative stress due to radiation exposure. In particular, the present invention relates to the use of glucosidic astaxanthin for the treatment of such oxidative stress.

2. Description of Related Art Including Information Disclosed Under 37 CFR 1.97 and 37 CFR 1.98

Astronauts aboard the International Space Station spend many consecutive months in space, and the face challenges that those on earth do not have to face. For example, the microgravity environment at the International Space Station places stress on the muscles and bones of the astronauts because the muscles and bones do not have to work as hard as they do on earth. On earth, the muscles and bones constantly experience a gravitational field. As a result, the muscles often atrophy unless the astronauts pay close attention to their nutrition and exercise regimens. In addition, the astronauts are constantly exposed to much higher levels of radiation than those on earth. This is because the astronauts aboard the International Space Station do not have the protection of the earth's atmosphere. This exposure causes organisms to generate Reactive Oxygen Species (ROS). ROS has long been found to play an important role in oxidative mediated DNA damage resulting from cosmic radiation. Fortunately, cells possess an antioxidant system that can neutralize ROS, in the form of glutathione and tocopherols. However, oxidative stress produced by cosmic radiation is so extensive that the organism is quickly overwhelmed by ROS or by impaired antioxidant pathways, thereby causing cell and organism death.

The closed environment and limited evasive capabilities inherent in spaceflight cause astronauts to be exposed to many potentially harmful agents, such as chemical contaminants and the environment and radiation exposure. Current power systems use to achieve spaceflight are prohibitively expensive for supporting the payload requirements to fully shield astronauts from cosmic radiation. Therefore, radiation poses a major, currently unresolvable risk for astronauts, especially for long-duration spaceflights. The major detrimental radiation effects that are a primary concern for long-duration spaceflights are damage to the lens of the eye, damage to the immune system, damage to the central nervous system, and cancer. In addition to the direct damage to biological molecules in cells, radiation exposure induces oxidative damage. Many natural antioxidants, whether consumed before or after radiation exposure, are able to confer some level of radioprotection. The current Risk of Exposure Death (% REID) is estimated at an unacceptable level of greater than 6%.

Astaxanthin is a xanthophyll of great interest in animal nutrition and human health. The market prospect in the nutraceuticals industries for this health-protective molecule is very promising. There is a current multi-billion-dollar demand for astaxanthin which increases it over 28% per year.

Astaxanthin is currently synthesized by several bacteria, algae and plants from beta-carotene by the sequential action of two enzymes: (1) a beta-carotene enzyme, 3,3'-hydroxylase that introduces an hydroxyl group at the 3 (and 3') positions of each of the two beta-ionone rings of beta-carotene, and a beta-carotene ketolase that introduces keto groups at carbons 4 and 4' of the β-ionone rings. Astaxanthin is also produced by the yeast-like basidiomycete *Xanthophyllomyces dendrorhous*. Carotenoids are an important group of naturally-occurring pigments with uses ranging from colorants, feed supplements and nutraceuticals. Carotenoids are also used for medical, cosmetic and biotechnological purposes. Although more than 600 carotenoids have been described from carotenogenic microorganisms, only beta-carotene, lycopene and astaxanthin are commercially produced by microbial fermentation. These three compounds have various biological functions such as species-specific coloration, light-harvesting, photo-protection, anti-oxidant, and hormone precursor. Dietary carotenoids have beneficial effects which delay the onset of many diseases such as arteriosclerosis, cataracts, age-related macular degeneration, multiple sclerosis, cardiovascular diseases, and some kinds of cancer. For these reasons, the demand and market of carotenoids have grown drastically.

Astaxanthin is a lipid-soluble keto-carotenoids having a deep red color. The high electronegativity of astaxanthin is a direct result of its hydroxyl and ketone functional groups (carboxylic acid groups) established on both ends of a carbon chain of alternating double bonds. This "dumbbell" shaped molecule has a central region of electrons that can be donated or adsorbed to reduce a reactive oxidizing molecule, such as PD-1, PD-L-1 and PD-L-2. Astaxanthin, unlike several carotenes and one other known carotenoid, is not converted to vitamin A (retinol) in the human body. Like other carotenoids, astaxanthin has a self-limited absorption orally and low toxicity. No toxic side effects have been observed. Astaxanthin is a free radical scavenger/antioxidant and is 400 times more reactive as an antioxidant than beta-carotene. Astaxanthin is not only the world's strongest natural antioxidant, astaxanthin is also a safe and natural anti-inflammatory. Astaxanthin is incredibly potent and well-rounded in its antioxidant activity. As a result, in an antioxidant test identified as "singlet oxygen quenching", astaxanthin has been shown to be 550 times stronger than vitamin A, 800 times stronger than CoQ10 and 6000 times stronger than vitamin C.

In the past various patent patents have issued with respect to the treatment and reduction of oxidative stress. For example, U.S. Pat. No. 8,937,099, issued on Jan. 20, 2015 to G. A. Goldstein, utilizes composition comprising N-acetyl-cysteine amide (NACA amide) and derivatives thereof. This NACA amide or derivatives thereof are administered alone, or in combination with other suitable agents, to reduce, prevent, or to counteract oxidative stress and free radical oxidant formation and overproduction in cells and tissues. It is also used provide a new source of glutathione.

U.S. Patent Application Publication No. 2018/0303767, published on Oct. 25, 2008 to G. M. Miller, describes a method of treating or suppressing oxidative stress diseases and symptoms related to oxidative stress affecting normal oxygen flow in cells caused by reactive oxygen species with redox-active therapeutics. The use of redox-active therapeutics serves to reduce, suppress or treat oxidative stress induced by chemical agents, such as contrast agents and other nephrotoxic agents, by radiation exposure, and by disruptions in the transport of oxygen to tissues.

U.S. Pat. No. 10,703,701, issued on Jul. 7, 2022 Hinman et al., discloses compounds and methods of using such compounds for treating or suppressing oxidative stress disorders, including mitochondrial disorders, impaired energy processing disorders, neurodegenerative diseases and diseases of aging, or for modulating one or more energy biomarkers, normalizing one or more energy biomarkers, or enhancing one or more energy biomarkers. The compounds are tocopherol quinone derivatives.

U.S. Pat. No. 9,464,106, issued on Oct. 11, 2016 to Mollard et al., teaches methods of treating or suppressing oxidative stress disorders affecting normal electron flow in cells. These oxidative stress disorders can include mitochondrial diseases, impaired energy processing disorders, neurodegenerative disorders, diseases of aging and diseases caused by reactive oxygen species. This method utilizes compounds such as catechol or ortho-quinone derivatives.

U.S. Pat. No. 9,707,239, issued on Jul. 18, 2017 to Kassis et al., discloses compounds that modulate oxidative stress. In particular, this invention provides methods of identifying compounds that selectively induce an oxidative stress response in a biological sample. This invention further provides methods of treating the subject having a disease associated with oxidative stress using compounds that are selectively induce an oxidative stress response in a subject.

U.S. Patent Application Publication No. 2003/0064955, published on Apr. 3, 2003 to Prasad et al., teaches the use of multiple antioxidant micronutrients as systemic biological radioprotective agents against potential ionizing radiation risks. This serves to protect humans in need of such protection from physical damage caused by ionizing radiation. This method comprises administering to such persons prior to and after exposure a plurality of antioxidants at a dosage level that directly proportional to the radiation level likely to be encountered.

In the past, various patents and patent publications have been directed to the production of astaxanthin. For example, U.S. Patent Publication No. 2010/0285557, published on Nov. 11, 2010 to Martin et al., pertains to a method for the efficient production of carotenoids. In particular, this invention is directed to a method for producing carotenoid and carotenoid-containing cells, especially astaxanthin and astaxanthin-containing cells, by generating mutant microorganisms belonging to the photoautotrophic algae of the class chlorophycealternative embodiment and culturing the same.

U.S. Pat. No. 7,063,957, issued on Jun. 20, 2006 to F. Chen, discloses a methods for producing ketocarotenoid astaxanthin by the green microalga *Chlorella zofingiensis* in dark-heterotrophic cultures so as to provide excellent growth and high-yield astaxanthin production on glucose-supplemented media in the dark.

U.S. Patent Publication No. 2005/0124032, published on Jun. 9, 2005 to De La Fuente Moreno et al., teaches a method of producing of astaxanthin by fermenting selected strains of xanthophyllomyces dendrorhous. These strains are selected based on: (i) resistance to inhibitors of steroid synthesis, to inhibitors of respiration and to compounds that induce the formation of free radicals; (ii) color intensity of the colony and production of carotenoids on solid medium; (iii) production of astaxanthin in darkness; (iv) production of astaxanthin in conditions with a raised temperature; and (v) production of astaxanthin with carbon sources other than glucose.

U.S. Patent Publication No. 2004/0077036, published on Apr. 22, 2004 to Thomas et al., provides a process to produce astaxanthin from haematococcus biomass. In particular, a modified nutrient medium containing four nitrogen sources is used for culturing the algae. Green motile cells produced are converted into dormant red cysts which are chilled and stressed for vigorous multiplication. Nutrients are added gradually and the initial germination is carried out without carbon dioxide sparging. The dilution stage is also effected in the absence of carbon dioxide. The stressed red cysts are regerminated and the cycle repeated to produce a biomass enriched with astaxanthin.

U.S. Pat. No. 6,022,701, issued on Feb. 8, 2000 to Boussiba et al., discloses a procedure for large-scale production of astaxanthin from haematococcus. In this process the haematococcus cells are cultivated under conditions suitable for optimal vegetative growth of such cells and the cells are collected and cultivated under conditions suitable for optimal induction and accumulation of astaxanthin in the cells. The cells are inoculating into a growth solution containing essentially a carbon source and growing the cells at a temperature of below 35° C.

It is an object of the present invention to provide a method for reducing oxidative stress due to radiation exposure.

It is another object of the present invention to provide a method for protecting astronauts against the exposure to cosmic radiation from long periods of time in space.

It is another object of the present invention to provide a method that reduces the risk of exposure death to an acceptable level.

It is still another object of the present invention to provide a method that reduces damage to the lens of the eye, damage to the immune system, damage to the central nervous system, and cancer in astronauts.

These and other objects and advantages of the present invention will become apparent from a reading of the attached specification and appended claims.

BRIEF SUMMARY OF THE INVENTION

The present invention is a method for treating the subject afflicted with oxidative stress. This method includes the steps of: (1) preparing glucosidic astaxanthin by reacting astaxanthin with a monosaccharide at a microwave frequency of between 1 and 100 GHz for at least one second and no more than 25 seconds; and (2) administering a therapeutic amount of the glucosidic astaxanthin to the subject in need of such treatment.

In the method of the present invention, the glucosidic astaxanthin has the following chemical structure:

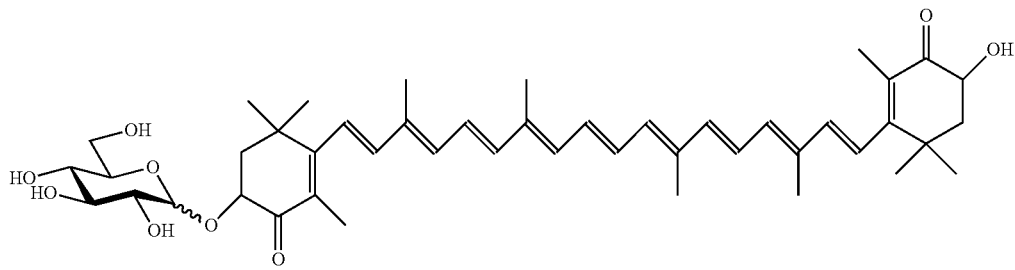

The step of administering includes adding the glucosidic astaxanthin to a carrier material. This character material can be edible. In particular, the carrier material can be either chocolate or an oil.

The therapeutic amount is greater than 0.1 mg per kilogram of body weight per day. In particular, the therapeutic amount is between 24 and 400 mg per kilogram of body weight per day. The glucosidic astaxanthin can be orally consumed or dermally applied. The dermal application of the glucosidic astaxanthin can be to an area of the skin where the subject is afflicted with oxidative stress.

Non-thermal plasma and ionizing cosmic radiation operate a common pathway to cell-killing effect, that is, ROS production. Non-thermal plasma generates the OH radical in gaseous form and transport transfers the radicals throughout the organism. Notably, the OH radical is a major mediator for DNA damage in cells under exposure to radiation of low linear energy transfer, such as x-rays and gamma rays. As a common physicochemical factor produced in plasma and radiation treatments, the OH radical production, as measured by High Sensitivity C-Reactive Protein indicates the extent of cellular exposures to plasma and radiation. The use of the glucosidic astaxanthin of the present invention demonstrates a dramatic reduction in human inflammatory response as measured by the High Sensitivity C-Reactive Protein. This implies that the oral application of the glucosidic astaxanthin reduces the ROS inventory and accumulation of free radicals. As such, it offers protection against the long-term effects of cosmic radiation exposure. The present invention, being a very potent antioxidant, can promote astronaut health aboard the International Space Station and generate tremendous long-term benefits, not only for the astronauts on board the International Space Station, but also for deep space travel.

This foregoing Section is intended to describe, with particularity, the preferred embodiments of the present invention. It is understood that modifications to these preferred embodiments can be made within the scope of the appended claims. As such, this Section should not be construed, in any way, as limiting of the broad scope of the present invention. The present invention should only be limited by the following claims and their legal equivalents.

DETAILED DESCRIPTION OF THE INVENTION

The present invention is a technique for administering glucosidic astaxanthin to a patient afflicted with oxidative stress due to radiation exposure. In particular, so as to achieve the benefits of the present invention, a therapeutic amount of the glucosidic astaxanthin is administered to the patient suffering the effects of oxidative stress. This glucosidic astaxanthin has the following chemical structure:

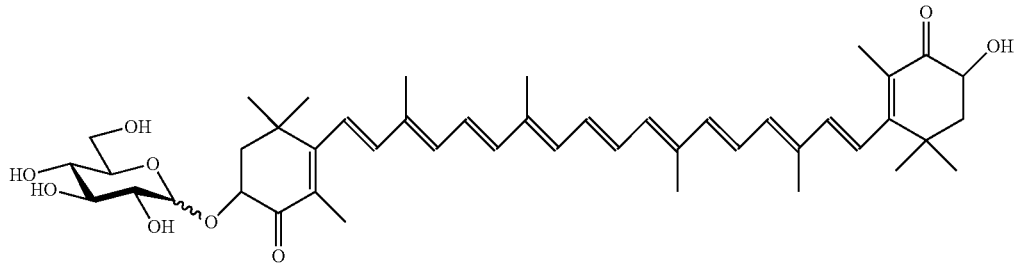

In order to administer the glucosidic astaxanthin, the glucosidic astaxanthin is added to a carrier material. Typically, this carrier material can be in the nature of a pill, an edible substance or an oil. In particular, the glucosidic astaxanthin can be added to a carrier material, such as chocolate. If the glucosidic astaxanthin is to be administered dermally, it can be added to an oil.

In order to achieve the advantages of the present invention, the therapeutic amount of the glucosidic astaxanthin should be greater than 0.1 mg per kilogram of body weight per day. Preferably, the therapeutic amount is between 24 and 400 mg per kilogram of body weight per day.

The glucosidic astaxanthin is prepared prior to the step of administering. In particular, the astaxanthin is reacted with a monosaccharide at a temperature so as to produce the glucosidic astaxanthin. In particular, the astaxanthin is reacted with a monosaccharide at a microwave frequency of between 1 and 100 GHz for at least one second and no more than 25 seconds.

The technology in which the glucosidic astaxanthin is effective in treating such oxidative stress is described hereinafter.

Clinical research conducted on the glucosidic astaxanthin of the present invention demonstrates that this glucosidic astaxanthin greatly inhibits oxidative stress, as measured by High Sensitivity C-Reactive protein, reduces hyperglycemic conditions, reduces Reactive Oxygen Species generated from radiation exposure, stops cancer cellular migration, and induces hypothesis in cancer cells. This glucosidic astaxanthin appears to block the PD-L1, IL-6 and NF-kb pathways. This reduces the proliferation of PD-L1 positive cancer cells and the inflammatory responses during and after radiation exposure. Incorporation of this glucosidic astaxanthin into biochemical nutritional therapy has been shown to reduce cancer formation and controls tumor growth and potentially reduces the impact of radiation exposure and associated side effects of Reactive Oxygen Species.

Experimental evidence shows that this glucosidic astaxanthin is an ACE-2 inhibitor and has protective effects on the tyrosine functional group of the ACE-2 receptor, thereby reducing viral cellular entry and reducing the cytokine storm caused by IL-6, NF-kb when administered at levels as high as fifty milligrams per kilogram of body weight per day. In addition, there is evidence that this glucosidic astaxanthin decreases oxidative stress and inflammation as measured by the High Sensitivity C-Reactive Protein reductions from as high as 66 to less than 3 in less than 10 days, which is a known accompaniment of radiation exposure. The role of oxidative stress in radiation exposure is well understood and is supported from observational studies that found associations between antioxidant intake, oxidative stress, and negative outcomes. Clinical intervention studies using antioxidants including vitamin E, beta-carotene and vitamin C have not proven successful due to the pro-oxidant effects. The glucosidic astaxanthin of the present invention is not a pro-oxidant and therefore does not contribute to inflammation. The antioxidants used, such as vitamin E, beta-carotene and vitamin C may not have been effective because insufficient doses were used, or in adequate length of therapy followed to correct the oxidative stress. Some antioxidant such as beta-carotene may be pro-oxidant at higher doses, which could have confounded study results and generated negative results or hepatic disease. The glucosidic astaxanthin of the present invention is a powerful non-pro-oxidant antioxidant with no safety concerns noted so far in human clinical studies where glucosidic astaxanthin has been administered at doses exceeding 500 mg per day in human trials. Since the glucosidic astaxanthin of the present invention is a potent antioxidant and is associated with membrane preservation, it protects against oxidative stress and inflammation associated with radiation-induced inflammatory-related diseases.

The generation of reactive oxygen species by radiation is one of the mechanisms through which radiation can manifest potential detrimental effects on health. When an imbalance develops due to ROS generation exceeding the body's antioxidant defense mechanisms, oxidative stress can develop causing cellular apoptosis and organism death.

Cosmic radiation and ionizing radiation operate a common pathway to cell-killing effect, that is, ROS production. Cosmic radiation promotes the OH radical in gaseous form and transfers the radicals systemically. The OH radical continues to play an important role in plasma medicine because of its higher oxygen potential and stronger disinfection power, as compared with other oxidative species. Notably, the OH radical is a major mediator for DNA damage in cells under exposure to radiation of low linear energy transfer, such as X-rays and gamma rays.

The use of the glucosidic astaxanthin of the present invention onboard deep space vehicles would reduce the Risk of Exposure Death to less than 3%. This can prove to be a determining factor in crew survival.

The foregoing disclosure and description of the invention is illustrative and explanatory thereof. Various changes in the details of the present invention can be made is the scope of the present claims without departing from the true spirit of the present invention. The present invention should only be limited by the following claims and their legal equivalents.

I claim:

1. A method of treating a subject of afflicted with oxidative stress due to radiation exposure, the method comprising:
   preparing glucosidic astaxanthin by reacting astaxanthin with a monosaccharide at a microwave frequency of between 1 and 100 GHz for at least 1 second and no more than 25 seconds; and
   administering a therapeutic amount of the glucosidic astaxanthin to the subject in need of such treatment.

2. The method of claim 1, the glucosidic astaxanthin having the following chemical structure:

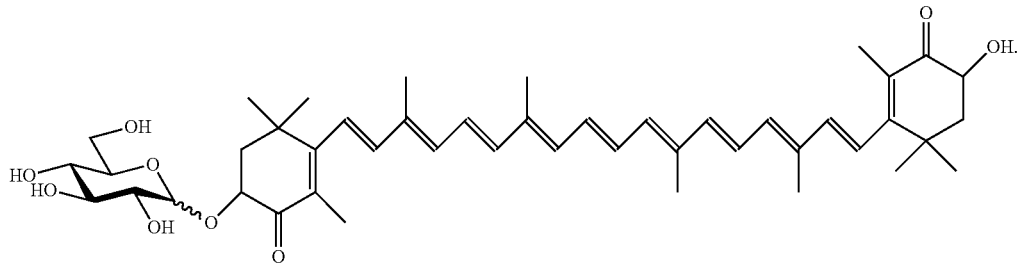

3. The method of claim 1, the step of administering comprising:
   adding the glucosidic astaxanthin to a carrier material.

4. The method of claim 3, the carrier material being edible.

5. The method of claim 4, the carrier material being chocolate.

6. The method of claim 3, the carrier material being an oil.

7. The method of claim 1, the therapeutic amount being greater than 0.1 milligrams per kilogram of body weight per day.

8. The method of claim 1, the therapeutic amount being between 24 and 400 milligrams per kilogram of body weight per day.

9. The method of claim 1, the step of administering comprising:
   orally consuming the glucosidic astaxanthin.

10. The method of claim 1, the step of administering comprising:

dermally applying the glucosidic astaxanthin onto an area of the skin where the patient is a afflicted with oxidative stress.

\* \* \* \* \*